United States Patent [19]

Davis et al.

[11] 4,093,859

[45] June 6, 1978

[54] AXIAL TOMOGRAPHIC APPARATUS

[75] Inventors: Gregory A. Davis, St. Charles; Kenneth E. Krippner, St. Louis; Jan A. Roestel, Ladue; Gottfried Vonk, Maplewood; Albert R. Zacher, Jr., University City, all of Mo.

[73] Assignee: Artronix, Inc., St. Louis, Mo.

[21] Appl. No.: 636,102

[22] Filed: Nov. 28, 1975

[51] Int. Cl.² .......................................... G01M 23/00
[52] U.S. Cl. .................................................. 250/445 T
[58] Field of Search ........................... 250/445, 445 T; 339/5 A

[56] References Cited

U.S. PATENT DOCUMENTS

| | | | |
|---|---|---|---|
| 2,711,519 | 6/1955 | Barrett | 339/5 A |
| 3,517,369 | 6/1970 | Buschbon | 335/5 A |
| 3,529,348 | 9/1970 | Kucharski | 339/5 A |
| 3,743,843 | 7/1973 | Reser et al. | 250/445 T |
| 3,778,614 | 12/1973 | Hounsfield et al. | 250/445 T |
| 3,790,782 | 2/1974 | Inoue et al. | 250/445 T |
| 3,881,110 | 4/1975 | Hounsfield et al. | 250/445 T |
| 3,924,131 | 12/1975 | Hounsfield | 250/445 T |
| 3,937,963 | 2/1976 | Hounsfield et al. | 250/445 T |

Primary Examiner—Bruce C. Anderson
Attorney, Agent, or Firm—Rogers, Eilers & Howell

[57] ABSTRACT

An x-ray tomography apparatus has a couch for a human subject to lie on, a cylindrical capsule to enclose part of the body, a flexible water filled bag to stabilize a portion of the human body being x-rayed, an x-ray source mounted on a rotatable frame, and an arcuate row of x-ray detector plates enclosed in a metal container filled with xenon gas. The detector plates are positioned on the rotatable frame opposite the x-ray source so that the x-ray pass through the subject and are received by the detector plates. The detector plates and x-ray source are continuously rotatable about the subject, having slip ring power and electrical connections. The couch is servo motor powered and is switched at the completion of one rotation of the rotatable frame to automatically index the subject forward. By continuous rotation of the x-ray source and detector plates and automatic indexing of the subject the continuous operation of the tomograph is possible and multiple observations on the subject can be made in a short time. The x-ray data obtained can be analyzed mathematically, e.g., by a computer program, and displayed in visual or numerical form by conventional techniques.

25 Claims, 19 Drawing Figures

AXIAL TOMOGRAPHIC APPARATUS

BACKGROUND AND SUMMARY OF THE INVENTION

This invention is related to apparatus for examining an object by means of radiation such as x or gamma radiation. More particularly, the invention is concerned with tomographic rotational examination which enables two dimensional x-ray examination to represent the three dimensional configuration of a thin tomographic slice. Tomography has been employed to examine parts of the human body, such as the head, to ascertain the location of tumors and extraneous or foreign matter.

Some of the prior art tomographic devices provide for rotation of an x-ray source and x-ray detectors about the portion of the object being examined. Some of the prior art devices which utilize rotation employ cables which limit the extent of possible rotation, and thus necessitate the expenditure of time and effort by a technician to readjust or reposition the cables so that the x-ray process can be continued. Rotation may be limited to as little as 180° in some devices. In other prior art devices, it is necessary for the x-ray technician or operator to manually adjust the position of the human body so that a different portion of the body can be x-rayed by a scan after a previous section has been scanned. Still other prior art devices have an x-ray source and x-ray detectors which are moved reciprocally relative to the body portion being examined, with their positions relative to the body portion being changed after each scan is taken.

Prior art devices have also taken x-ray slices of thicknesses of eight millimeters or greater. The thickness of prior slices made it difficult to detect pathological tissue or other irregularites in tissue structure. It is difficult to compensate for the great amount of normal tissue included in a slice of eight millimeters thickness when the data from the slice is analyzed. As a result, displayed representations of the slice, either visual or numerical, are not entirely satisfactory. The averaged normal tissue tends to obscure the presence of abnormal structure.

The present device has considerable advantages over the prior art. The new device is continuously rotatable in one direction. Consequently there is no need to reposition or readjust cables for each rotation and the examination proceeds considerably faster. In addition, the subject is automatically repositioned with each complete rotation so an examination sequence of several rotations and examination "slices" can be conducted in sequence continuously. The x-ray source is pulsed many times as the x-ray source and detector are rotated around the subject. Each pulse constitutes an examination of the subject. One rotation of the device then provides a great quantity of data which can be analysed to provide a more accurate model of the examined subject. The x-rays are projected in a thin beam, allowing greater discrimination between observed structure, as described in the reference *Neurological CAT System* by Artronix Incorporated, incorporated herein by reference.

Even with the thinner scan, the time of a complete examination sequence for a subject such as a human head is considerably reduced. The time for each scan is reduced due to the continuous mode of operation of the device and the pulsed series of examinations in each rotation. The subject is automatically indexed forward at the completion of each rotation of the device and a new scan proceeds. As a result of the increased speed per scan and the increased speed between scans in a sequence, the total examination time for a subject is greatly reduced, with greater accuracy. As a result a tomograph machine can be used to examine more subjects, such as human patients, per day with less cost in capital investment and labor per examination.

DESCRIPTION OF THE PREFERRED EMBODIMENTS

Figures 1, 17:
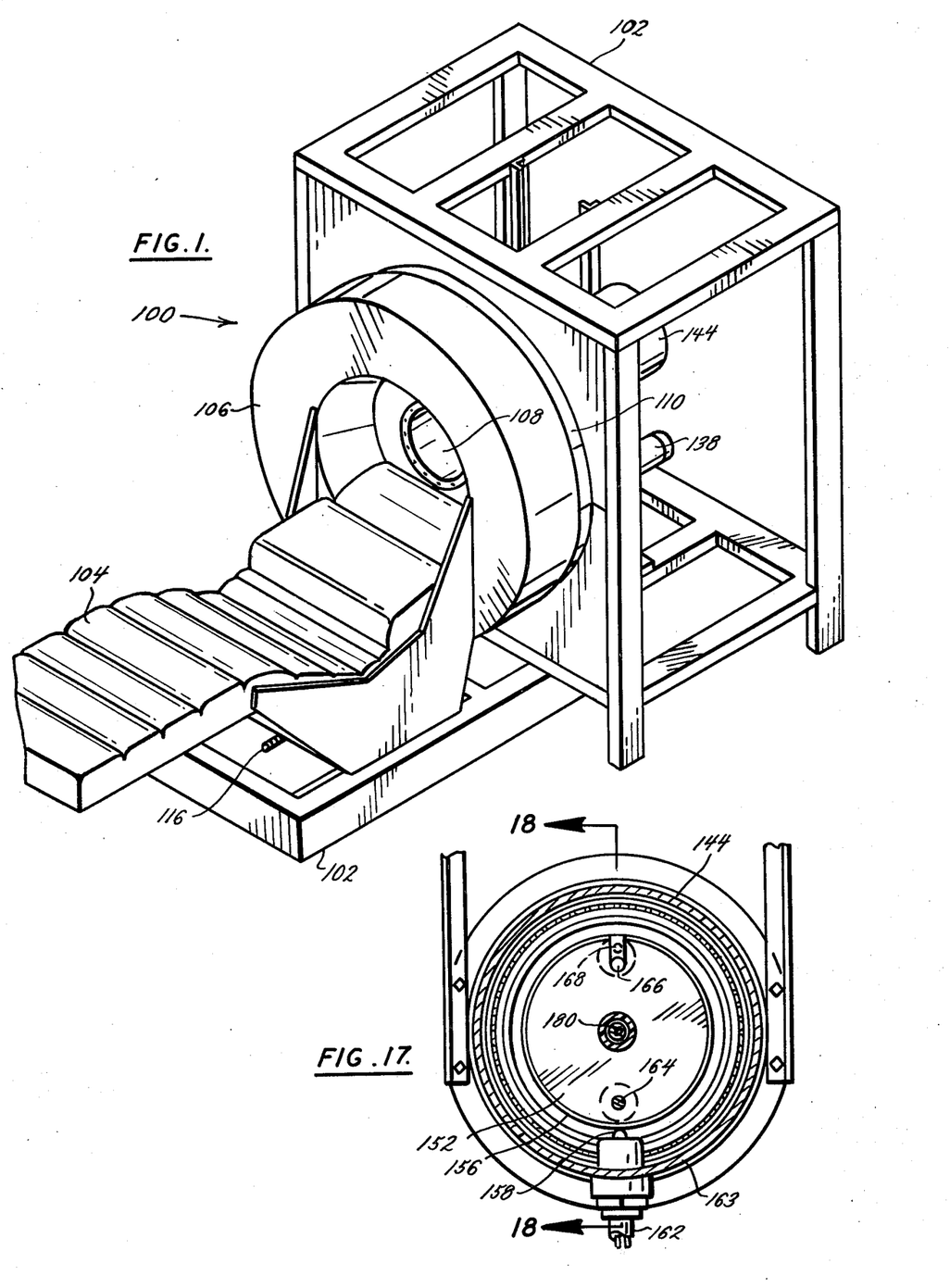
FIG. 1 is an isometric view of the x-ray tomograph.
FIG. 17 is a cross-sectional view of the power connection tank taken along the plane of lines 17—17 in FIG. 2.

Referring in more detail to the drawings in FIG. 1, the complete axial x-ray tomograph 100 is shown. The tomograph 100 has a basic frame structure 102 which supports the tomograph. The tomograph 100 has a movable couch 104 supported in the frame 102. The couch 104 is connected with a shield 106 and a head tank 108 which receives the head of a subject to be x-rayed. Shield 106 overlaps a rotatable support 110 and the head tank 108 projects through the center of the rotatable support 110, as shown. Rotatable support 110 is mounted on ball bearings 112 in a mounting plate 114 attached to frame 102.

Figures 2, 18:
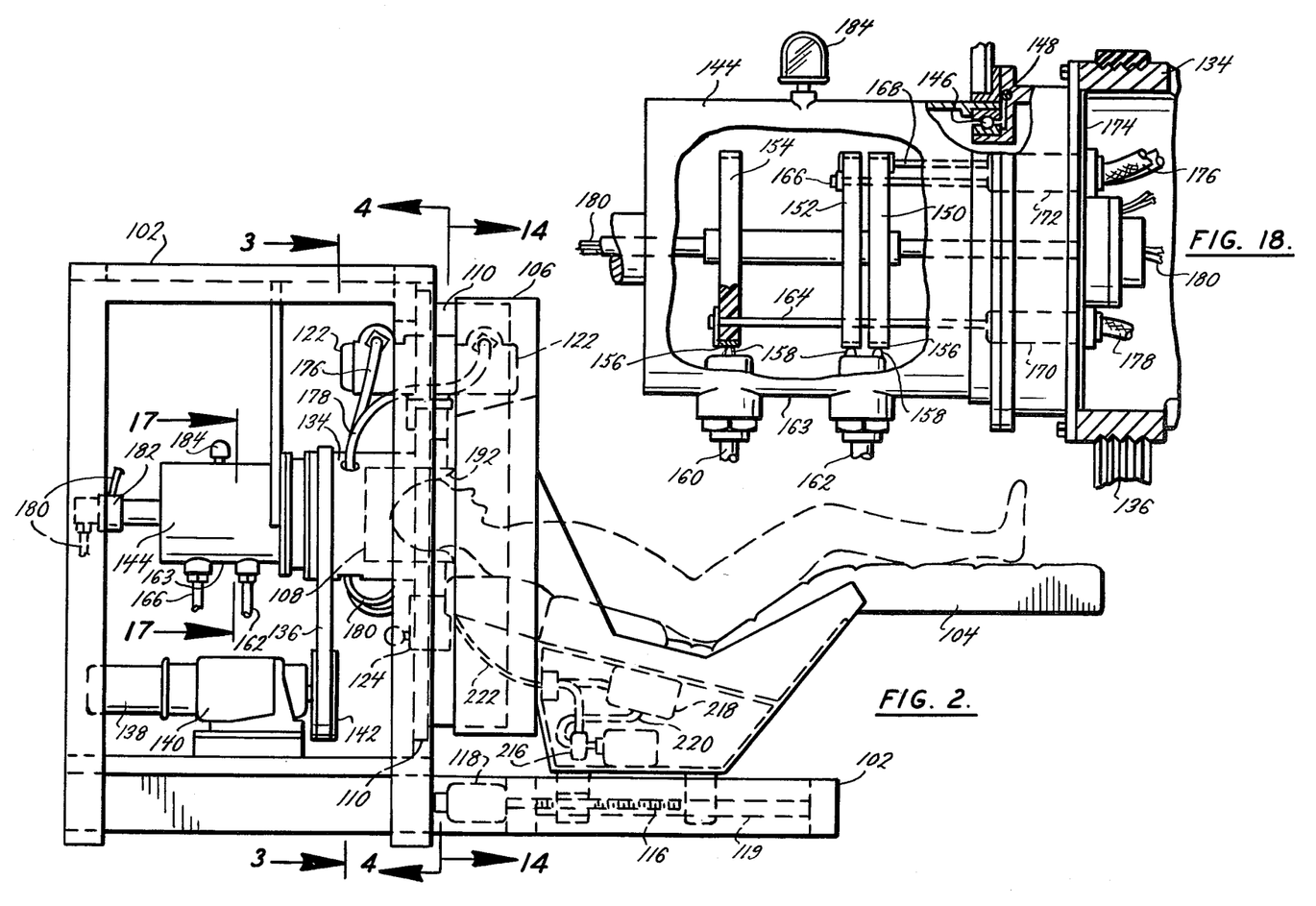
FIG. 2 is a longitudinal sectional view of the tomograph shown in FIG. 1.
FIG. 18 is a longitudinal sectional view of the power connection tank taken along the plane of lines 18—18 in FIG. 17.
Figure 3:
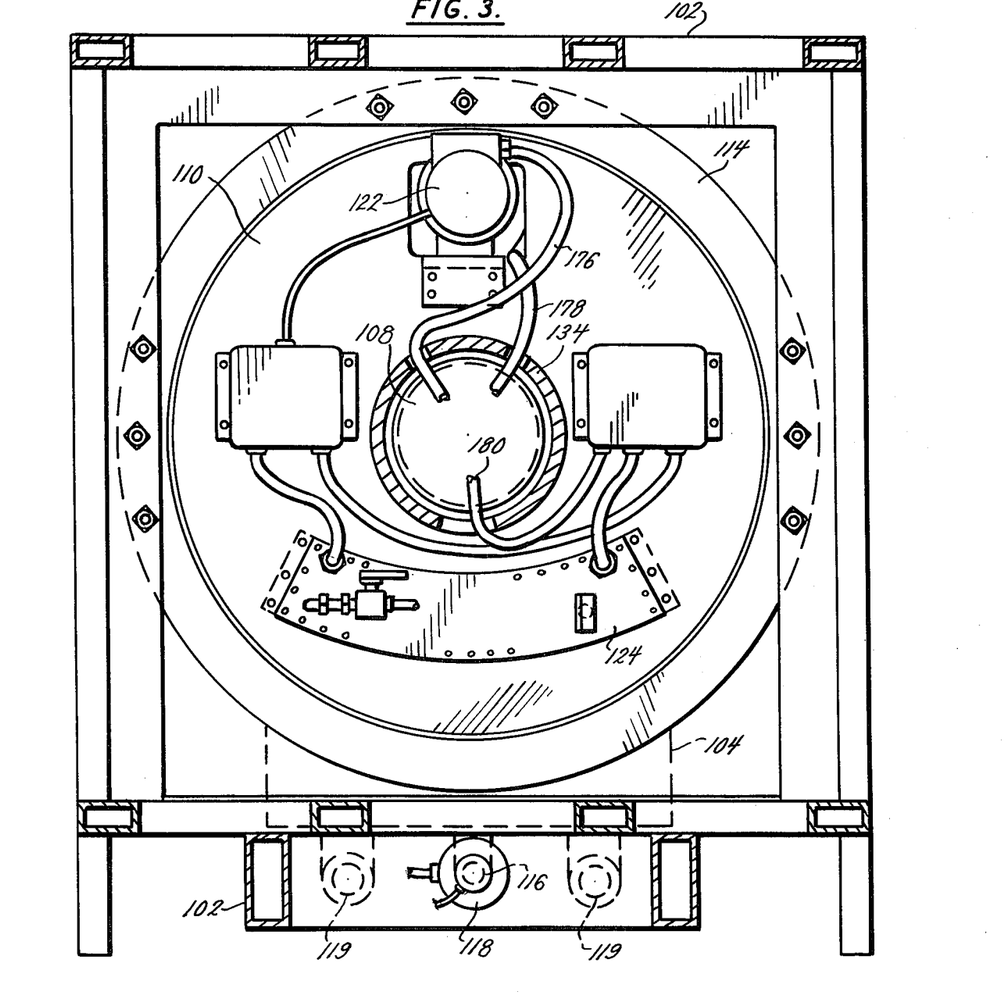
FIG. 3 is a cross sectional view of the tomograph taken along the plane of lines 3—3 in FIG. 2.

Couch 104 is mounted in frame 102 and driven by lead screw 116, shown in FIGS. 2 and 3. Lead screw 116 is driven by servo motor 118 which, in response to a signal, can reciprocally position the couch 104 along sliding supports 119. Couch 104, shield 106 the head tank 108 reciprocate relative to rotating support 110 with head tank 108 positioned within opening 120 in the rotating support 110. Rotating support 110 rotates concentrically about the horizontal axis of head tank 108 as is described herein.

Figure 4:
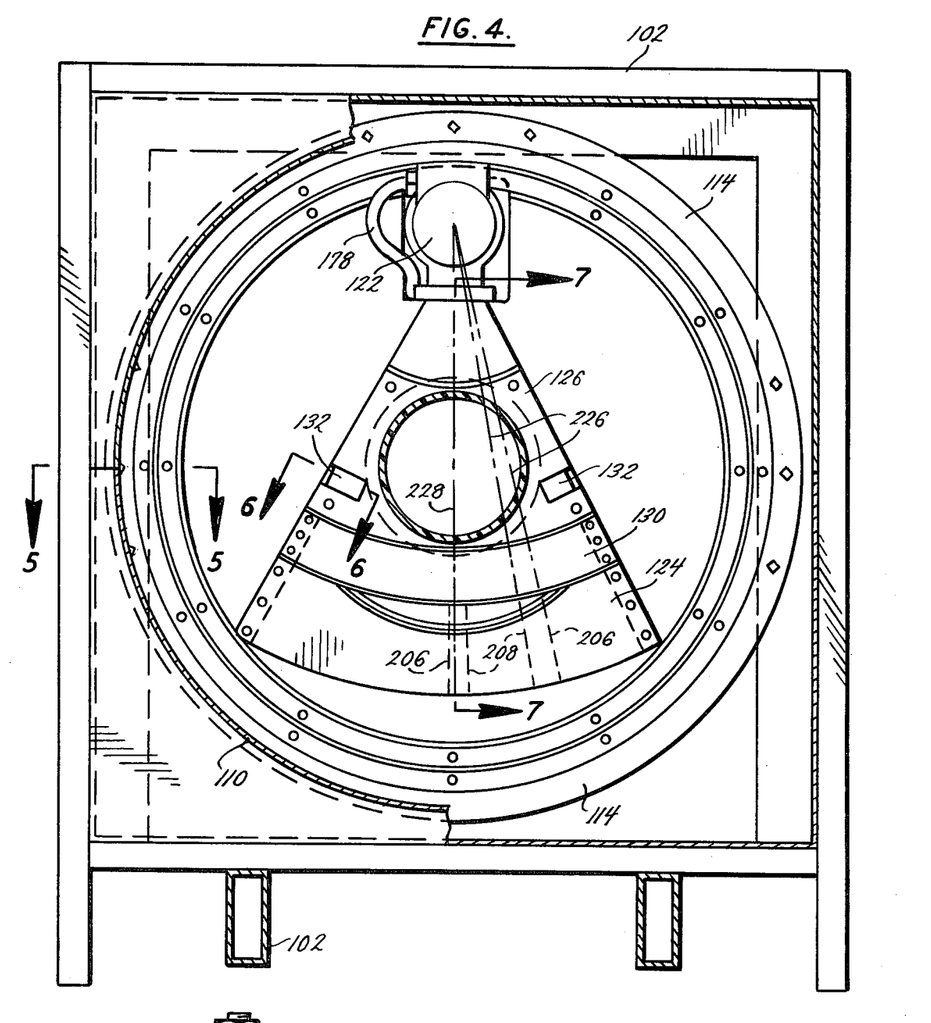
FIG. 4 is a cross sectional view of the tomograph taken along the plane of lines 4—4 in FIG. 2.
Figure 5:
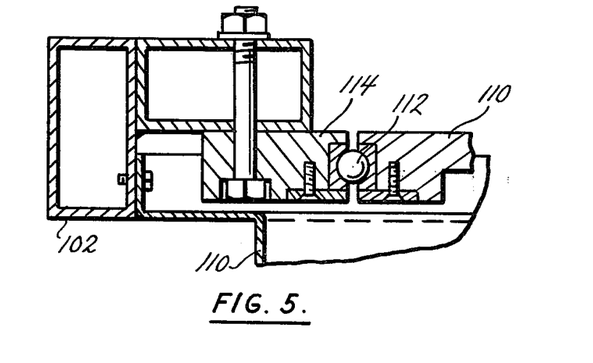
FIG. 5 is a partial cross sectional view of the tomograph taken along the plane of lines 5—5 in FIG. 4.
Figure 6:
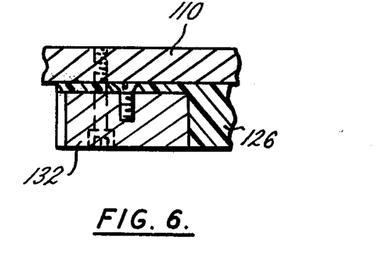
FIG. 6 is a partial cross sectional view of the energy discrimination blocks for the tomograph taken along the plane of lines 6—6 in FIG. 4.
Figures 7, 8, 9:
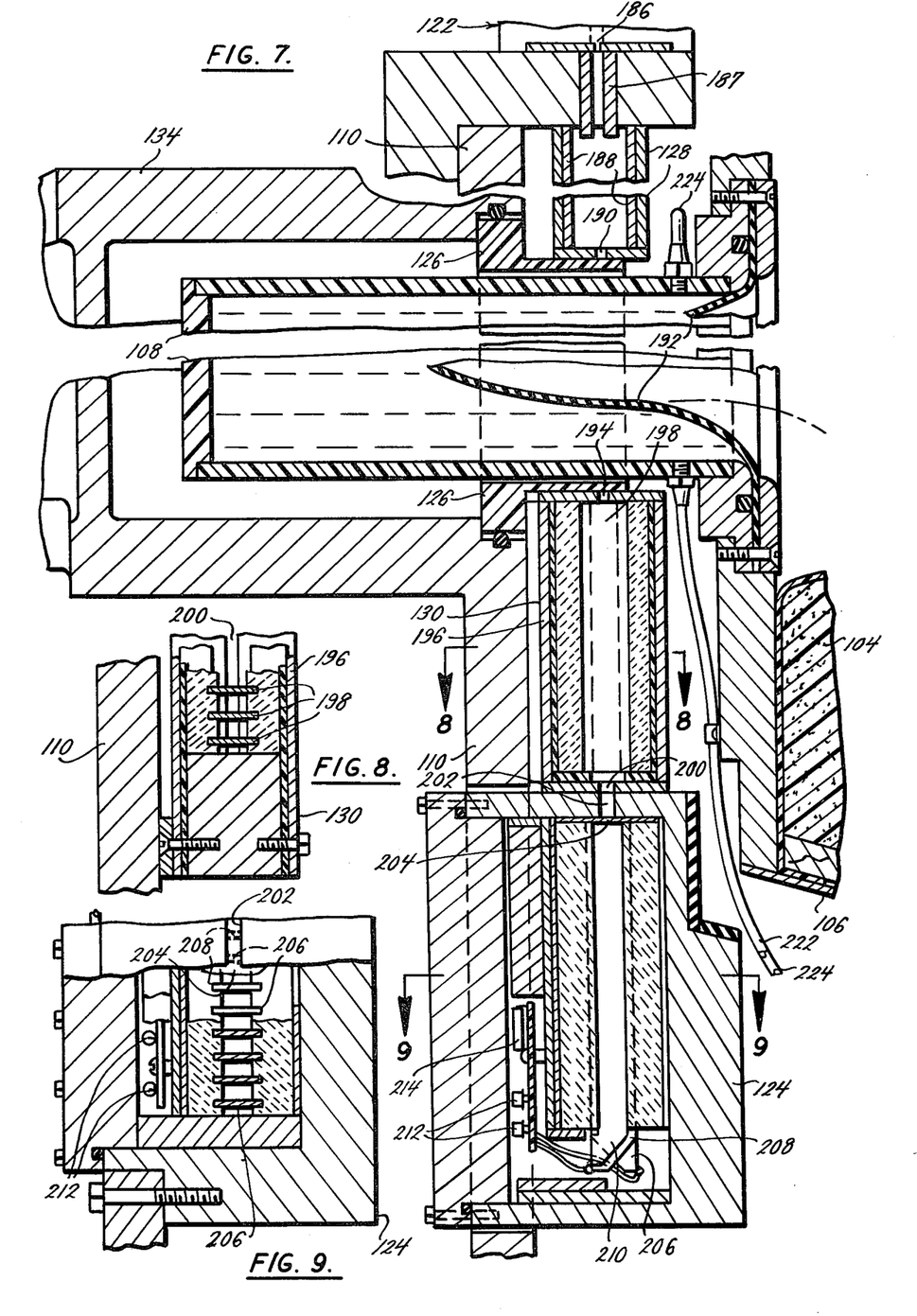
FIG. 7 is a broken cross sectional view of the tomograph taken along the plane of lines 7—7 in FIG. 4 showing portions of the x-ray source, slit collimator, head tank, scatter collimator, and detector.
FIG. 8 is a broken cross-sectional view of the scatter collimator taken along the plane of lines 8—8 in FIG. 7.
FIG. 9 is a broken cross-sectional view of the detector taken along the plane of lines 9—9 in FIG. 7.

Near an edge of rotating support 110 and along a diameter of support 110 is mounted an x-ray tube 122, as shown, for rotation with rotating support 110. Near the opposite edge of rotating support 110 and substantially bisected by the diameter on which x-ray tube 122 is mounted, is an x-ray detector 124, as shown. The rotating support 110 in the area between the x-ray tube 122 and detector 24 is relieved, as shown in FIG. 4, to receive head tank 108. Surround head tank 108 is an acrylic field 126. Slit collimator 128 is spaced above acrylic field 126 at a location between acrylic field 126 and the x-ray tube 122. Positioned between acrylic field 126 and detector 124 is scatter collimator 130.

Acrylic field 126 has two energy discrimination blocks 132 at the outer edges of field 126, as shown. Energy discrimination blocks 132 allow detector 124 to measure the energy of the x-ray beam. The detector cells lying along the path of the beam passing through blocks 132 measure the amount of attenuation of the beam by blocks 132 and allow compensation for the attenuation characteristics of the x-rays as a function of the energy of the x-rays. Detector 124 may also contain suitable field strength detectors, not shown.

On the side of rotatable support 110 opposite couch 104 and fixed centrally to the rotatable support 110 and concentric about head tank 108 is drive boss 134. Drive boss 134 is driven through belt 136 by the combination of motor 138, transmission 140 and sheave 142. Drive boss 134 connects to power housing 144 by bearings 146 and rotatable seal 148 so that the boss 134 can rotate while power housing 144 remains stationary. Power housing 144 contains rotating slip ring electric power connectors 150, 152 and 154 which rotate with rotating boss 134 and rotatable support 110.

Slip rings 150, 152 and 154 are of non-conducting material, e.g., an acrylic or other suitable plastic, and have conducting metal rings 156 on their periphery. Power for x-ray tube 122 is supplied through spring-biased contacts 158 and cables 160, 162 which pass through the wall 163 of power housing 144. Metallic conductors 164, 166 and 168 conduct the power through seals 170, 172 and the back wall 174 of rotating boss 134 and then via cables 176, 178 to x-ray tube 122.

Additional conductors 180 pass centrally through power housing 144 through a sealed low power slip ring connection 182, as shown. Conductors 180 supply connections to the control mechanism, such as a digital computer, e.g., an Artronix, PC12 (TM) which controls the operation and functions of the tomograph. Conductors 180 supply the power connections to the detector 124 and for certain auxiliary functions of the tomograph, if desired, as will be appreciated by those skilled in the art. Power housing 144 is filled with transformer oil, not shown, to prevent arcing of the high voltage power supply to the x-ray tube, and has a sight glass 184 for the transformer oil which also serves as an expansion chamber.

The structure of x-ray source 122, slit collimator 128, head tank 108, scatter collimator 130 and detector 124, are shown in more detail in FIGS. 7–12. X-ray tube 122 is of conventional design, but is equipped with a lead disc primary collimator having a slit in the form of a lead disc having a rectangular slot window 186 through which the emitted x-rays can pass in roughly a fan-shaped planar beam. The beam passes through primary shield 187 into the adjoining rectangular slit collimator box 128, which is lined with lead 188, and which has a slit 190 which again collimates the x-ray beam into a thin planar fan-shaped beam. The beam passes through the adjacent acrylic field 126 mounted on rotatable support 110 and through acrylic head tank 108 received therein. Head tank 108 is filled with water in use. The water is retained in head tank 108 by a latex rubber cap 192 which fits closely around the head of the subject.

From the object the x-ray beam passes through the bottom of head tank 108 and through slit 194 into scatter collimator 130, mounted on rotatable support 110, as shown. Scatter collimator 130 has a lead lining 196 and scatter collimator plates 198 which lie radially along the x-ray beam. The source of the x-rays in x-ray tube 122 is the center of curvature for the radii on which plates 198 lie. As shown, the scatter collimator 130 contains one hundred thirty-two collimator plates 198. The angle between adjacent collimator plates 198 is 0.342°. Scatter collimator 130 absorbs scattered radiation passing through the subject and allows only radiation which has been collimated to lie on radii extending from the source of the radiation in x-ray tube 122 and in the plane of thin slot 200 at the base of scatter collimator 130 to enter slot 202 of detector 124. Detector 124 is mounted on rotatable support 110 adjacent to scatter collimator 130, as shown. The collimated radiation then passes through window 204 in detector 124 where it is absorbed by xenon or other conventional ionizable gases, and is detected on plates 210 of detector 124 as charged ions.

The structure of the detector, apart from the tomograph claimed herein, is not claimed in the instant application but is described herein for purposes of illustration. The various structure of the detector is disclosed and claimed in the co-pending applications Ser. No. 636,101 of of Kenneth E. Krippner and Albert R. Zacher, Jr., entitled X-RAY DETECTOR filed Nov. 28, 1975, co-pending herewith, and Ser. No. 636,704 Albert R. Zacher, Jr., entitled AXIAL TOMOGRAPHIC APPARATUS AND DETECTOR, filed Nov. 28, 1975, co-pending herewith.

The detector 124, as is scatter collimator 130, is roughly a truncated fan-shaped box. Detector 124, as shown, also contains one hundred thirty-two plates. The plates intersect the plane of the x-ray beam and lie along radii aimed at the point source of the x-ray beam as shown. Detector 124 contains an atmosphere of xenon, not shown, at ten atmospheres absolute pressure. Due to the mechanical requirements of connecting the detector and the presence of other detector components, normally only one hundred twenty-eight measurements are taken by the cells defined by the plates 206, 208, 210.

Figures 10, 11, 12, 13, 14:
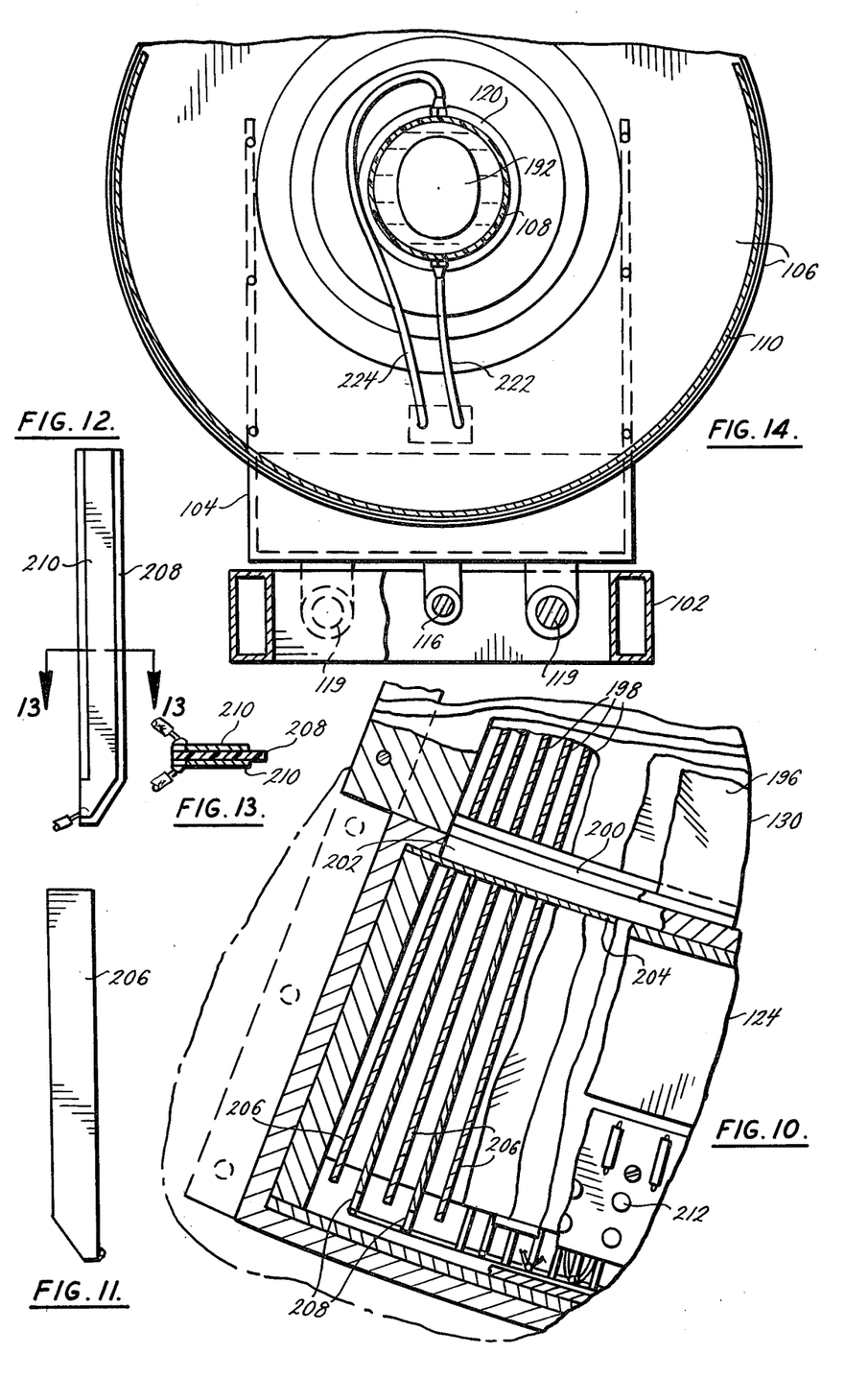
FIG. 10 is a broken sectional view of the scatter collimator and detector.
FIG. 11 is a front plan view of a reference plate used in the detector.
FIG. 12 is a front plan view of a collector plate composite used in the detector.
FIG. 13 is a cross-sectional view taken along the plane of lines 13—13 in FIG. 12.
FIG. 14 is a cross-sectional view of the tomograph taken along the plane of lines 14—14 in FIG. 2.
Figure 16:
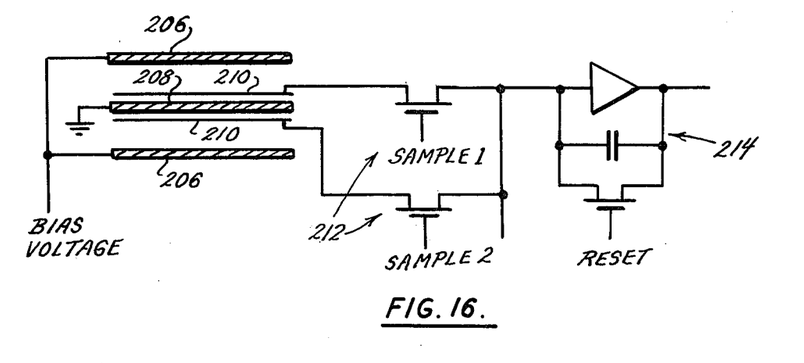
FIG. 16 is a circuit diagram of the detector switching and amplifier circuit.

The plates in detector 124 are an alternating series of plates 206 and 208. Plates 206 are reference plates and are maintained at a potential of minus 3 kilovolts relative to ground potential. Plates 208 also are reference plates and are maintained at ground potential. As shown in FIG. 12, Plates 208 have adhered thereon a thin polyethylene terephthalate (mylar TM) plate 210 on which there is a thin coating of vaporized aluminum. However, any thin conductor, such as copper foil or its equivalent, on an insulating substrate would be satisfactory. Plates 210 are connected, through a series of sequentially firing electronic switches 212, to an integrating amplifier circuit 214. Amplifier circuit 214 is connected via wiring hardware, not shown, to the controlling switching station, but preferably to an Artronix PC-12 (TM) digital computer, or other conventional computer. FIG. 16 shows the amplifier circuit for the signals received from plates 210.

As shown in phantom in FIG. 4, the detector plates 206 and 208 lie along radii 226 which have the point source of the x-radiation as their common center of curvature. The scale of the plate placement is enlarged in FIG. 4 for greater clarity. As is also shown in FIG. 4, the plates are located in the detector so that a radius 228 which passes through the axis of rotation support 110, and thus through the center of the object examined in head tank 108, does not lie along any of plates 206 and 208.

The detector 124 and plates 206, 208 are located so that the radius 228, generated at the point source of the x-radiation in x-ray tube 122 and passing through the axis of rotation of rotatable support 110 and through the center of the object in tank 108, passes between plates 206 and 208 at a location which does not bisect the distance between plates 206 and 208. The preferred location for radius 228 is onefourth the distance between plates 206 and 208, as shown.

By spacing the plates so that radius 228 passes onefourth the distance between plates 206 and 208 greater spatial resolution is obtained in collecting the data in a single scan. The detector spaces between adjacent plates scan beams which intercept adjacent toroidal areas of the object and which progressively overlap from edge to center of the object. By spacing the detector plates as described, the area of the object scanned by any one detector space, also is overlapped during a single rotation. In effect, a single scan of 360° rotation will take overlapping observations of the observed slice during one rotation giving resolution equivalent to a scan of 180° rotation with detectors spaced at intervals one-half as great. The finer resolution of the observations increases the accuracy of subsequent analysis of the data. If the detector plates are placed symetrically about the radius which passes through the center of the object, one-half of the detector is redundant over a 360° scan. There is duplication of data, rather than overlap, and resolution is only one-half as good.

Figure 15:
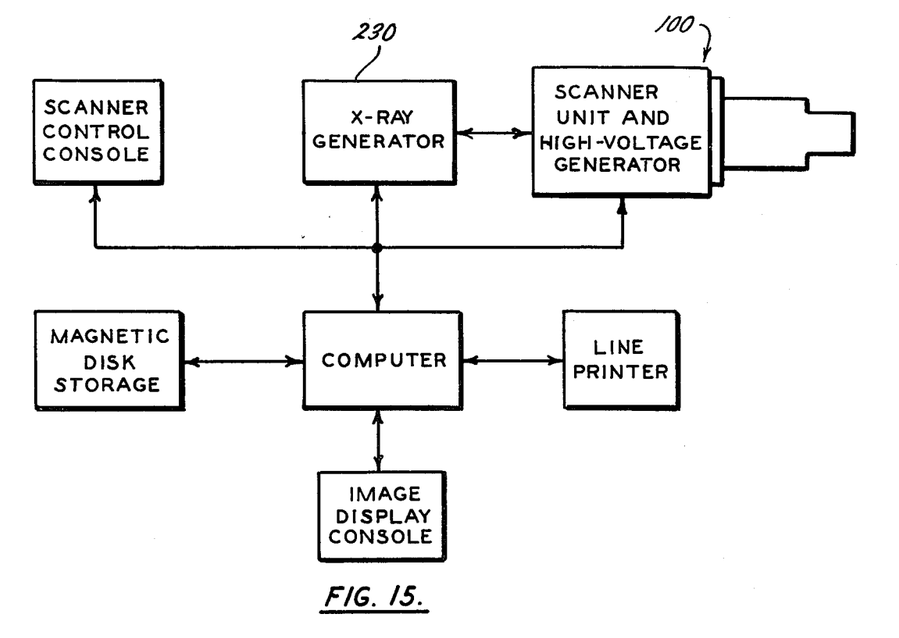
FIG. 15 is a block diagram of the x-ray and scanner unit with supporting equipment.

FIG. 15 shows the general layout of the tomographic scanner and its auxiliary equipment such as the controlling digital computer, for example, an Artronix PC-12(TM), or other conventional digital computer, suitably programmed.

As shown in FIG. 2, additional equipment included in the tomograph are a water pump 216 connected to a reservoir 218 via tubing 220 and also to head tank 108 via tubes 222 and 224.

Figure 19:
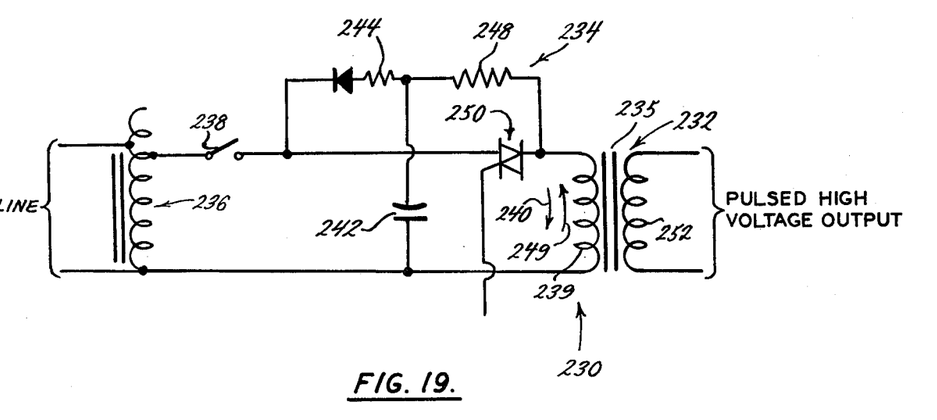
FIG. 19 is a circuit diagram of the x-ray pulsing and switching circuit.

The x-ray generator 230, as shown in FIGS. 15 and 19, controls the pulsing of x-ray tube 122. X-ray generator 230 has a transformer 232 and a direct current biasing circuit 234 to bias the core 235 of transformer 232 to prevent magnetic saturation of the transformer core 235.

As shown schematically in FIG. 19, an auto transformer 236 receives sixty cycle line voltage to compensate for variations in the line voltage. When mechanical switch 238 is closed (when the machine 100 is activated), biasing circuit 234 applies a substantially level direct current across the transformer primary windings 239, as shown by arrow 240. The filter capacitor 242, surge limiting resistor 244, and current limiting resistor 248 are preferably chosen to provide a current equal to the transformer magnetization current and of opposite sign to the current of the first half cycle. On initiation of operation of the machine 100, rotation of rotatable support 110 is started and after the biasing circuit has been connected across the primary windings 239 of the high voltage transformer 232, the control mechanism (preferably the Artronix PC-12 TM computer) signals electronic switch 250 to fire the x-ray tube 122. The 60 cycle line voltage is conducted to the primary windings 239 of the transformer 232 initially in the direction opposite to biasing current provided by biasing circuit 234, as shown by arrow 249. The electronic switch 250 closes for one complete cycle, allowing one cycle of voltage across primary windings 239 of high voltage transformer 232, which is transformed into a one cycle high voltage output in the secondary windings 252 of the transformer and is conducted to x-ray tube 122 to provide a short pulse of x-rays.

The biasing circuit 234 assists in reducing the total current across the electronic switch 250 so that the switch will disconnect the primary windings 239 of transformer 232 from the line voltage. The switch 250 then waits until a subsequent signal is sent by the controlling mechanism, the computer, that is, for one complete cycle.

The use of biasing circuit 234 is also valuable, since if high voltage transformer 232 is cycled repeatedly without the bias, the core 235 will become magnetically saturated. If the core 235 becomes saturated, it will not pass any additional voltage into the secondary windings 252 of the transformer 232 and the transformer 232 would fail to pulse the x-ray tube 122. The effective resistance across the primary windings 239 would become very small and the current across the primary windings 239 would then become dangerously high. Biasing circuit 234 prevents the saturation of the core 235 of the transformer 232 by creating an initial magnetization of opposition polarity and by allowing sufficient time between cycles for the magnetization of core 235 to equilibrate.

Other means for pulsing x-ray tube 122 may be used if desired, provided that a suitable rapid pulsing and scanning is obtained.

The structure of the x-ray pulsing means is not claimed in the instant application, but is described herein to illustrate a pulsing means. The structure of the pulsing means is disclosed and claimed in the co-pending application of Kenneth E. Krippner entitled HIGH SPEED X-RAY PULSING DEVICE, filed Nov. 28, 1975, co-pending herewith.

Operation of the Device

It will be appreciated that various operations of the x-ray tomograph could be controlled by an operator who initiates each function by a series of conventional electrical switches connected to motor drives and servo motors, or by relay switches on the rotating support 110 and other portions of the machinery, which on completion of a rotation energize various servo circuits. However, it is preferred that the entire function of the machine, once started, be controlled by a suitable computer program through a conventionally programmable digital computer, such as the Artronix PC-12(TM) or other conventional computer. A suitable program is currently available and is used for this purpose by Artronix, Incorporated of St. Louis, Missouri, but one skilled in the art would easily devise a suitable program from the following description of the machine functions, for example, by using FORTRAN programming techniques such as are taught in *Introduction to FORTRAN,* by Daniel McCracken (McGraw-Hill).

To examine a patient, using the apparatus disclosed and claimed herein, the patient is positioned in a prone position as shown in phantom in FIG. 3, with the patient's head firmly fixed inside latex cap 192. Latex cap 192 expands, when pump 216 pumps water out of head tank 108 into reservoir 218, thus creating a partial vacuum in head tank 108, making insertion of the patient's head a simple matter. When the head is properly positioned inside latex cap 192, water is pumped from reservoir 218 back into head tank 108 collapsing latex cap 192 closely around the subject's head.

When the subject is suitably positioned in the device, the motor 138 is energized starting rotation of rotating support 110 and high voltage power is supplied to the x-ray tube 122. The x-ray tube is pulsed for very short durations two hundred fifty-six times in the course of one complete 360° rotation. Normally one rotation will be completed in nine seconds or less. At the end of one complete rotation, the servo motor 118 is energized indexing the patient forward, that is in a direction to the right as shown in FIG. 2. The patient is moved a distance of approximately three millimeters, the approximate width of the x-ray beam, and a new scan is started. Depending on the power used in the x-ray beam and the time between scans required to cool the x-ray equipment, as many as three or more discrete full power examinations of 360° each can be completed within one minute. This is much faster than conventional equipment which may require about five minutes to complete two scans. A typical examination of a patient can require less than five minutes.

Since the detector takes one hundred twenty-eight measurements per pulse and the x-ray source is pulsed from two hundred fifty-six separate positions in one 360° rotation of the tomograph, there are 32,768 total measurements taken in each 360° rotation of the device. The valve measured is the attenuation of the x-ray beam which passes into the detector. These attenuation measurements are subjected to non-cartesian (polar) analysis by means of the digital computer in a 256 × 256 matrix, so that each word of data represents the absorbtion value for a volume of analyzed tissue that is one millimeter by one millimeter by three millimeters (the thickness of the x-ray beam). While it would be possible to use the successive approximation technique disclosed by U.S. Pat. No. 3,778,614, the specification of which is included herein by reference, it is preferred that an algebraic transformation be used which takes advantage of the non-cartesian geometry of this measurement system. A suitable transformation is that of A. M. Cormack, "Representation of a Function by its Line Integrals, With Some Radiological Applications II", published in the *Journal of Applied Physics,* v. 35, No. 10, October, 1964.

The attenuation of the x-ray beam is preferably measured on an arbitrary scale in which the attenuation of water is zero; the attenuation of air is −500 and the attenuation of dense bone is approximately +500. The attenuation of the acrylic head tank 108 and field 126 are also essentially zero, as is the value for normal soft tissue. This scale improves the precision of the computation in analyzing the data obtained, since a simple null comparison can be made and any deviation from the null analyzed.

The strength of the attenuated radiation is measured by detector 124. After the radiation from x-ray tube 122 is collimated into a thin fan-shaped beam by slot 186 and slit collimator 128 it passes through the subject and through acrylic head tank 108, through the surrounding water, not shown, in head tank 108, and through field 126. The beam is collimated in collimator 130 to eliminate the scattered radiation and passes into the detector 124. There the x-rays ionize the xenon gas, not shown, present in the detector 124. The strength of the charge of the ionized gas is proportional to the strength of radiation passing into the detector 124. The ionized xenon travels to plates 210 where the charge is read through switches 212 and integrator-amplifier circuit 214 and digitized by an analog to digital converter, not shown. The digital valve is stored in a digital computer or other device. The switches 212 are set to fire sequentially so that only one amplifier circuit 214 is needed to transmit the data into computer storage.

Energy discrimination blocks 132 enable the detector 124 to measure the energy of the x-ray beams so that the attenuation characteristics of the matter x-ray beam can be calculated and small variations and artifacts can be eliminated. The energy attenuation function of x-rays is well known to those skilled in the art and the computer program having the attenuation characteristics built in could be easily produced by those skilled in the art. Such a program is currently produced by Artronics, Inc.

The data obtained is analyzed mathematically by operation of the computer and can be printed out in numerical form and stored by conventional means, either tape or disc, for on-line printers and similar equipment. Additional peripheral or storage equipment, i.e., video, can be provided, as is well known to those skilled in the art. The data can be collected by full power scanning of individual slices and displayed per individual slice or can be collected on low power scanning and a plurality of slices averaged and analyzed to produce one display, as required by the particular radiological examination being conducted.

It will be appreciated by those skilled in the art that many other variations and modifications may be made of the apparatus and methods disclosed herein without departing from the spirit of the invention. It is expected that the invention is not to be limited by the disclosure incorporated herein for purposes of illustration, but is limited only by the scope of the appended claims.

We claim:

1. An apparatus for examination of an object having a support, means to position an object to be examined in cooperation with the support, an x-ray source mounted on the support, an x-ray detector mounted on the support in a cooperating relationship with the x-ray source and an object, the detector being positioned to receive x-rays emanating from the x-ray source and passing through the object, means to rotate the support about the object, and means providing power connections to the apparatus, the power connection means being capable of supplying power through continuous rotation of the rotating means in one rotational direction.

2. The apparatus of claim 1 wherein the apparatus has means responsive to the rotating means to reposition the object in response to the rotating means.

3. The apparatus of claim 1 wherein the rotating means has means to rotate through an angle of at least 360°.

4. The apparatus of claim 1 wherein the rotating means has means to continuously rotate in one rotational direction.

5. The apparatus of claim 2 wherein the repositioning means is responsive to reposition the object on completion of a complete rotation of the rotating means.

6. A method of thin slice axial tomography comprising generating a thin fan-shaped planar beam of x-rays, passing the beam through an object, collimating the scatter from the beam passing through the object and detecting the attenuation characteristics of the beam, the generating of the beam and detection of its attenuation characteristics being conducted while continuously rotating the x-ray source and detector about the axis of the object the beam being pulsed during the course of rotation, automatically repositioning the object on completion of one complete rotation of the beam and detector about the object to sequence a subsequent adjacent examination of the object by continuing rotating the x-ray source and detector about the axis of the object while pulsing the x-ray source to generate additional pulsed thin fan-shaped planar beams which pass through an adjacent portion of the object, collimating those beams passing through the object to eliminate scatter and detecting the attenuation of the beam, and continuously supplying power to the x-ray source and detector as they are rotated about the object through continuous sequential rotations in one rotational direction to provide a continuous series of examinations throughout rotation in said one direction.

7. The apparatus of claim 1 wherein the power connecting means is a slip ring means.

8. The apparatus of claim 1 wherein the apparatus has means to collimate the x-rays enamating from the x-ray source.

9. The apparatus of claim 1 wherein the apparatus has means to collimate the x-rays passing through the object.

10. The apparatus of claim 2 wherein the means to reposition the object is a servo motor means responsive to the rotation of the rotating support.

11. An x-ray tomograph apparatus for cranial tomography comprising a frame, a rotatable support mounted in the frame, a central opening means in the support for receiving an object, means on the frame mounting a tank within the opening means for reciprocal movement into and out of the opening in a direction perpendicular to the plane of the rotatable support, adjustable means to position an object, with a portion of the object in the tank, an x-ray source mounted near one edge of the rotatable support with a means to project a thin fan-shaped beam of x-rays substantially parallel to the rotatable support and along a diameter thereof and through an object positioned in the tank, a first collimator means positioned between the x-ray source and the tank and capable of collimating the beam of x-rays into a thin fan-shaped beam, a detector placed near the extremity of the rotatable support opposite the x-ray source and being on the diameter on which the beam of the x-ray source is projected, the detector being capable of receiving a beam of x-rays emanating from the x-ray source a passing through an object in the tank; a second collimator means located between the head tank and the detector and being capable of eliminating scatter radiation from the x-ray beam passing through the object, means to rotate the rotatable support continuously in one rotational direction being located in the frame and connected to the rotatable support, means providing power connections to the apparatus, the power connection means being capable of supplying power and control connections through continuous uni-directional rotation of the rotatable support, the apparatus having mounted in the frame a servo motor and gear means responsive to the rotation of the rotatable support to selectively reposition the object in the tank for successive examinations, the apparatus having an x-ray field defining means surrounding the tank and spaced between the first and second collimator means, the field defining means having field strength detector means, the apparatus having mounted in the frame a reservoir for fluid and a pump means by which the tank can be selectively filled and emptied of the fluid, the tank having a flexible seal means to receive an object and isolate the object from the fluid.

12. The apparatus of claim 11 wherein the apparatus has means to pulse the x-ray beam.

13. The apparatus of claim 11 wherein the x-ray beam is collimated to a thin beam of about 3 millimeter thickness.

14. The method of claim 6 wherein the pulse beam is generated as a thin fan-shaped planar beam of about 3 millimeters thickness.

15. The method of claim 6 wherein the beam passing through the object is collimated to be substantially linear and spaced along radii having their center of curvature at the point of generation of the x-ray beam.

16. The method of claim 6 wherein the attenuation values of the detected x-ray beam are analyzed numerically to provide a representation of the internal structure of the object.

17. The method of claim 6 wherein the beam is pulsed 256 times in one 360° rotation of the x-ray source.

18. The method of claim 6 wherein rotation is continued in the original rotational direction.

19. The method of claim 6 wherein a plurality of rotations are conducted sequentially.

20. The method of claim 1 wherein on complete rotation is conducted in approximately 9 seconds.

21. The method of claim 1 wherein a plurality of complete rotational sequences is conducted in approximately 5 minutes.

22. The device of claim 1 wherein the means for providing power connections comprises a stationary container, rotatable means connected to the container at one extremity of the container and free to rotate relative thereto, means sealing the connection between the rotatable means and the container, power transmitting means in the container, the power transmitting means being connected with the rotatable means and rotatable therewith, power supply means passing through the container and cooperating with the power transmitting means to supply power thereto, means in the container insulating the power supplying and power transmitting means.

23. The device of claim 22 wherein the power transmitting means is a plurality of rotatable discs and the power supplying means is a plurality of sliding connectors cooperating with the discs.

24. The device of claim 23 wherein the discs are in insulating material and gave conducting rings on the periphery of the discs, the discs having power connections passing through the discs and cooperating with the rings.

25. The apparatus of claim 1 wherein the means to rotate the support about the object comprises a cylindrical case adapted to be mounted thereon at an edge of the cylinder, the junction between the edge of the cylinder and the cover having a bearing spaced between the cover and the cylinder and a rotatable seal sealing the junction of the cover and the cylinder, a plurality of insulating discs are positioned in the cylinder and are disposed concentrically about the axis of the cylinder, the discs are connected to the rotatable cover for rotation about the axis of the cylinder in cooperation with the rotatable cover, the discs are of an insulating material and have conducting rings fixed about their periphery, the discs having a plurality of conducting busses passing through the discs for rotation therewith and joining the conducting rings, the busses passing through the rotating cover and connecting with external power connections, the busses being sealed in the rotatable cover, the cylinder having means passing through a wall of the cylinder forming slip connectors, the slip connectors being placed in a cooperating relationship with the conducting rings of the rotating discs to form a sliding connection between the connecting means and the disc when the disc rotates with the rotating cover to establish a sliding continuous electrical contact therewith, whereby a continuous electrical connection through the power connection means is maintained when the rotatable cover and discs are rotated continuously, the cylinder having means to contain an insulating fluid and having means to determine the level of that fluid, the cylinder having additional means passing axially through the cylinder and the discs therein and through the rotatable cover for electrical contact, the additional means also having slip ring connections.

* * * * *

UNITED STATES PATENT OFFICE
CERTIFICATE OF CORRECTION

Patent No. 4,093,859    Dated June 6, 1978

Inventor(s) Gregory A. Davis, Kenneth E. Krippner, Jan A. Roestel Gottfried, Vonk, Albert R. Zacher, Jr.

It is certified that error appears in the above-identified patent and that said Letters Patent are hereby corrected as shown below:

The word "valve" in line 19 of column 8 should be - value -.

The numeral "1" in line 42 of column 10 should be -6- .

The numeral "1" in line 44 of column 10 should be -6- .

The word "pulse" in column 10, line 25, should be -pulsed- .

Signed and Sealed this

Twenty-ninth Day of January 1985

[SEAL]

Attest:

DONALD J. QUIGG

Attesting Officer    Acting Commissioner of Patents and Trademarks